US00PP21422P3

(12) United States Plant Patent
Ho

(10) Patent No.: US PP21,422 P3
(45) Date of Patent: Oct. 26, 2010

(54) *PHALAENOPSIS* PLANT NAMED 'P.HO'S COLOURFUL BUBBLES'

(50) Latin Name: ***Phalaenopsis* sp.**
Varietal Denomination: P. Ho's Colourful Bubbles

(75) Inventor: Tin-Fan Ho, Taipei (TW)

(73) Assignee: Ting-Jung Liu, Hualien County (TW)

( * ) Notice: Subject to any disclaimer, the term of this patent is extended or adjusted under 35 U.S.C. 154(b) by 0 days.

(21) Appl. No.: 12/321,177

(22) Filed: Jan. 19, 2009

(65) Prior Publication Data

US 2010/0186133 P1 Jul. 22, 2010

(51) Int. Cl.
*A01H 5/00* (2006.01)

(52) U.S. Cl. ..... Plt./311

(58) Field of Classification Search ..... Plt./311
See application file for complete search history.

*Primary Examiner*—Kent L Bell
(74) *Attorney, Agent, or Firm*—Muncy, Geissler, Olds & Lowe, PLLC

(57) ABSTRACT

A new and distinct cultivar of *Phalaenopsis* plant named '*P.* Ho's Colourful Bubbles', particularly characterized by its attractive and unique light green flowers with light pink shaded petals, freely flowering habit, freely branching and thick flowering stems, and strong growth ability.

2 Drawing Sheets

Botanical classification: *Phalaenopsis* sp.

Variety denomination: '*P.* Ho's Colourful Bubbles'.

The present invention relates to botanical classification/cultivar designation: *Phalaenopsis* Orchid cultivar *P.* Ho's Colourful Bubbles.

BACKGROUND OF THE INVENTION

The present invention comprises a new and distinct cultivar of *Phalaenopsis* Orchid, and hereinafter referred to by the cultivar name, '*P.* Ho's Colourful Bubbles'.

The new cultivar is a product of a planned breeding program conducted by the inventor in Hualien, Taiwan. The objective of the breeding program is to create new uniform pot-type *Phalaenopsis* Orchid cultivars having attractive flower coloration.

The new cultivar breeder was Tin-Fan Ho. The new cultivar was discovered by the inventor from within the progeny of a cross-pollination of two identified proprietary selections of *Phalaenopsis* Orchid, not patented, in April, 1998, in a controlled environment in Taiwan. Later, it was verified and registered in Royal Horticulture Society (R.H.S.) and had its variety name "*P.* Ho's Colourful Bubbles" on September 2001.

Asexual propagation by tissue culture in a laboratory in Hualien, Taiwan has been used to increase the number of plants for evaluation and has demonstrated that the unique combination of characteristics as herein disclosed for the new *Phalaenopsis* Orchid are firmly fixed and are retained through successive generations of asexual reproduction.

SUMMARY OF THE INVENTION

The following traits have been repeatedly observed and are determined to be basic characteristics of '*P.* Ho's Colourful Bubbles' which, in combination, distinguish this *Phalaenopsis* Orchid as a new and distinct cultivar:

1. Light green flowers with light pink shaded petals.
2. '*P.* Ho's Colourful Bubbles' has much more branches and flowers than other green *Phalaenopsis*.

3. Strong growth ability and disease resistance.
4. A compound raceme inflorescence and thick flowering stem.

Plants of the new cultivar differ primarily from plants of the parent cultivars in the flower color. In particular, the flower color of parent '*P.* Ho's Little Caroline' is white with red stripe and the flower color of parent '*P.* Dou-dii Golden Princess' is yellow with red spots, whereas the flower color of '*P.* Ho's Colourful Bubbles' is green.

Plants of new *Phalaenopsis* Orchid can be compared to plants of the culture *P.* Fortune Saltzman 'Maple Bridge' (not patented), differing from plants of the cultivar *P.* Fortune Saltzman 'Maple Bridge' in the following characteristics:

1. Plants of the new *Phalaenopsis* Orchid are bigger than plants of the cultivar *P.* Fortune Saltzman 'Maple Bridge'.
2. Plants of the new *Phalaenopsis* Orchid have more branches and flowers than plants of the cultivar *P.* Fortune Saltzman 'Maple Bridge'.
3. Plants of the new *Phalaenopsis* Orchid have more roots than plants of the cultivar *P.* Fortune Saltzman 'Maple Bridge'.
4. Plants of the new *Phalaenopsis* Orchid have stronger disease resistance than plants of the cultivar *P.* Fortune Saltzman 'Maple Bridge'.
5. The natural flowering *Phalaenopsis* Orchid is from February to June, whereas the natural flowering season of *P.* Fortune Saltzman 'Maple Bridge' is from April to June, in the northern part of Taiwan.
6. Plants of the new *Phalaenopsis* Orchid have compound raceme inflorescences and the *P.* Fortune Saltzman 'Maple Bridge' has solitary inflorescences.
7. Plants of the new *Phalaenopsis* Orchid have rhombate-shaped petals, and *P.* Fortune Saltzman 'Maple Bridge' has elliptical-shaped petals.

BRIEF DESCRIPTION OF THE DRAWINGS

Colors in the photographs may appear different from the color values that appear in the detailed botanical description which more accurately describe the new cultivar.

DETAILED DESCRIPTION OF THE PREFERRED EMBODIMENTS

Figure 1:
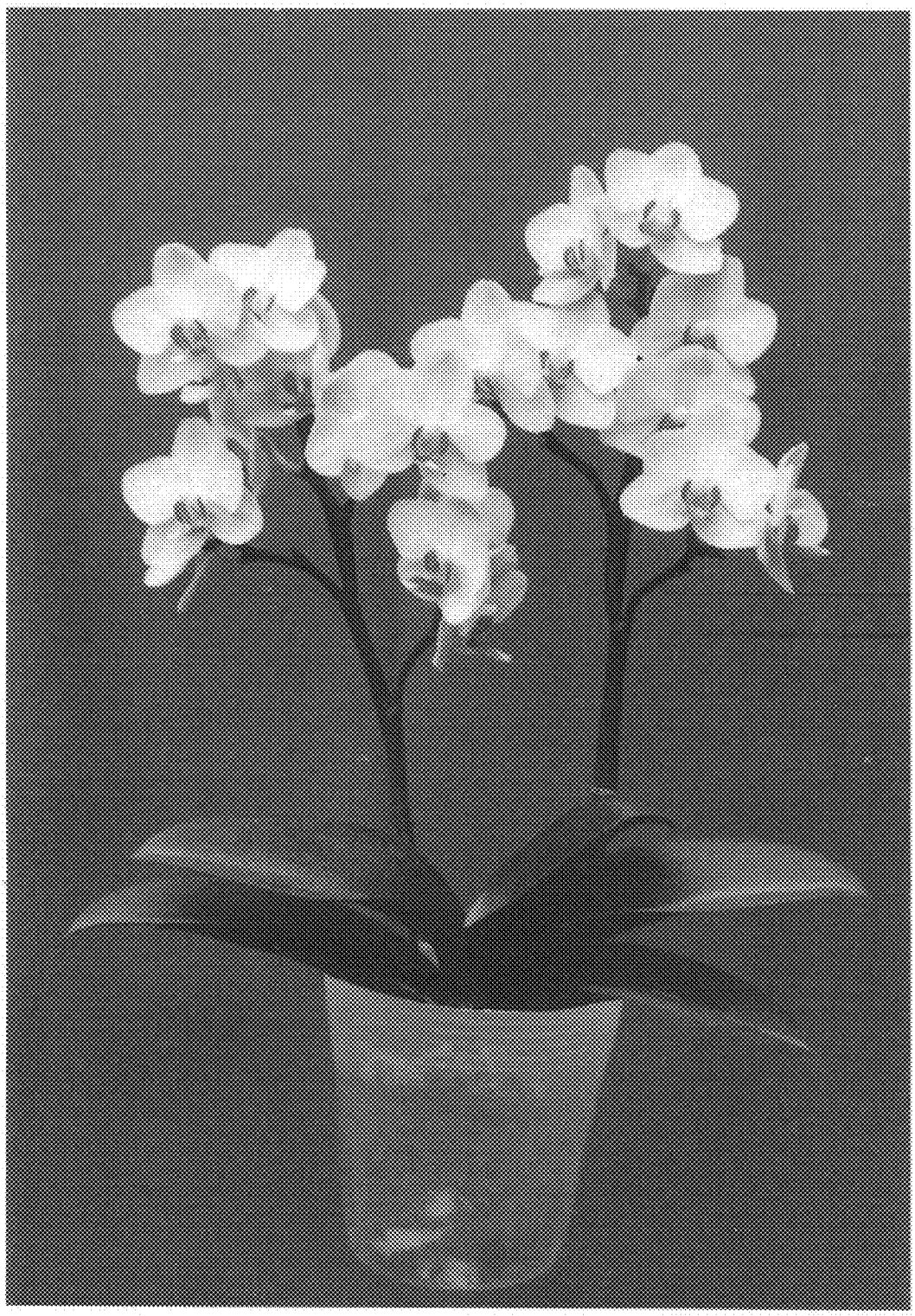
FIG. 1 is a side view of a plant of '*P*. Ho's Colourful Bubbles' flowering in the pot of 13 cm.
Figure 2:
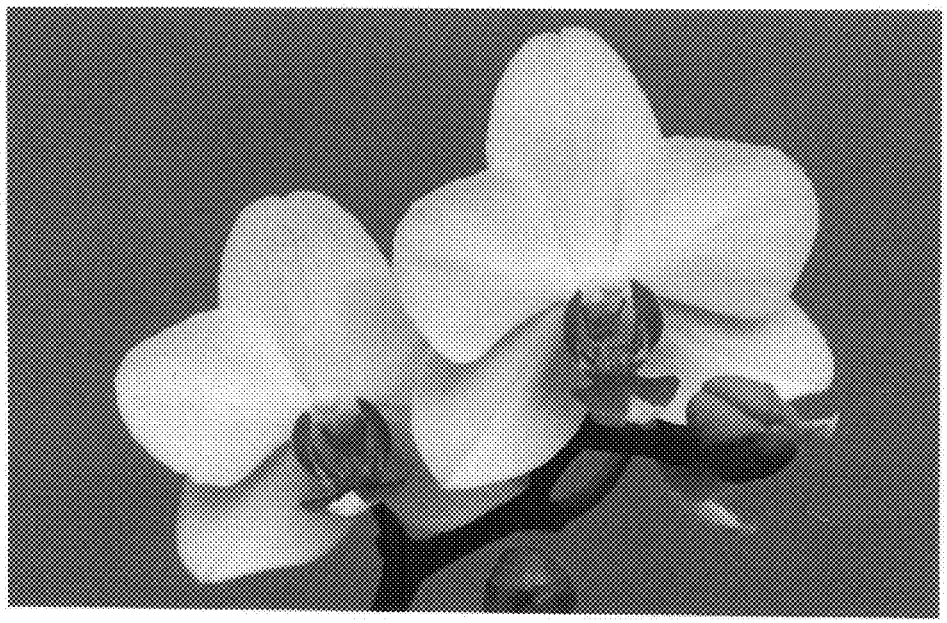
FIG. 2 is a close-up view showing the characteristics of the flower.
Figure 3:
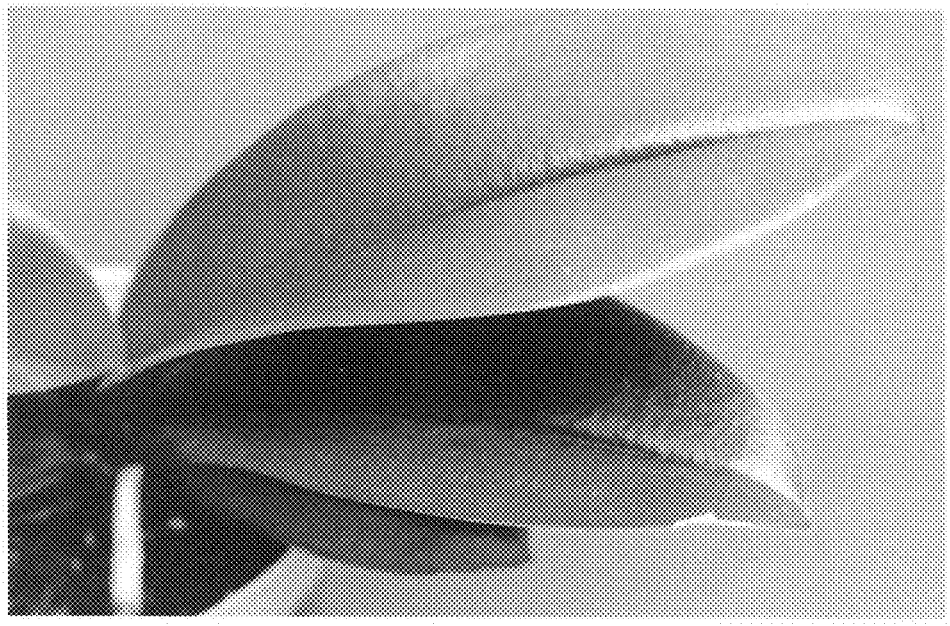
FIG. 3 is a close-up view showing the characteristics of the leaf.

'*P*. Ho's Colourful Bubbles' has not been observed under all possible environmental conditions. The phenotype may vary significantly with variations in environment such as temperature and light intensity, without however, any change in genotype. In the following description, color references are made to The Royal Horticultural Society (R.H.S.) Colour Chart, except where terms of ordinary dictionary significance are used.

Plants used for the aforementioned photographs and following detailed botanical description were 12 months old and grown in 13 cm, in Hualien, Taiwan, in a controlled greenhouse with day temperatures about 18 to 32° C., night temperatures about 18 to 32° C., and light levels about 11,000 to 16,000 lux. The photographs and the detailed botanical description were taken from February to April.

Parentage:

*Seed.*—*P*. Ho's Little Caroline, not patented. Pollen: '*P*. Dou-dii Golden Princess', not patented.

*Propagation.*—Asexual propagation by tissue culture.

Plant description:

*Plant shape.*—Two-ranked leaves affixed to a short central stem (monopodial growth). Single flowers arranged on upright and sturdy flowering compound racemes.

*Plant height, soil level to top of foliar plane.*—About 10 to 15 cm.

*Plant height, soil level to top of inflorescences.*—About 35 to 40 cm.

*Plant diameter.*—About 25 to 30 cm.

*Flowers per stem.*—Approximately 20 to 60.

Foliage description:

*Arrangement.*—Alternate.

*Quantity per plant.*—About 8 to 9.

*Length.*—About 15 to 18 cm.

*Width.*—About 5.8 to 7.3 cm.

*Shape.*—Oblong.

*Apex.*—Oblong.

*Base.*—Oblong.

*Margin.*—Entire.

*Aspect.*—Mostly flat and folded upward from the midrib.

*Texture, upper and lower surfaces.*—Glabrous.

*Venation.*—Parallel.

*Color.*—(*upper surface*).—RHS 131A.

*Color.*—(*lower surface*).—RHS 135C.

Flower description:

*Flower type.*—Single zygomorphic flowers, roughly pentagonal in shape.

*Flower arrangement.*—Compound racemes.

*Flowering stems.*—Upright, freely branching, thick, 30 to 40 cm in length, green (RHS 131A), and with a 0.7 to 0.9 cm diameter.

*Flowering habit.*—Plants freely flowering; plants typically produce four to eight branched flowering stems with at least 20 to 30 flowers each.

*Fragrance.*—Flowers not fragrant.

*Self-cleaning or persistent.*—Flowers self-cleaning.

*Rate of flower.*—Flowers could bloom at the same time.

*Natural flowering season.*—From February to June in the northern part of Taiwan. The flower spikes can be induced under a controlled environment, with a day/night temperature of 25/18° C. for 3 weeks.

*Post-production longevity.*—Plants of the new *Phalaenopsis* Orchid maintain good leaf and flower substance for about two to four months on the plant under interior environmental conditions. Inflorescence length: About 30 to 40 cm.

*Inflorescence diameter.*—About 20 to 30 cm.

*Flower diameter.*—About 6 to 6.5 cm.

*Flower depth.*—About 2.5 cm.

*Flower shape.*—Orbicular.

Flower bud description:

*Flower bud shape.*—Bud apex is orbicylar and bud base is ovate.

*Flower bud opening rate.*—Flower buds can all open in one week in sunny conditions.

*Flower bud length.*—About 2 cm.

*Flower bud diameter.*—About 1.8 cm.

*Flower bud color.*—About RHS 154D.

Petals:

*Quantity.*—Two per flower.

*Length.*—About 2.8 cm.

*Diameter.*—About 2.8 cm.

*Shape.*—Rhombate.

*Apex.*—Rhombate.

*Base.*—Obovate.

*Margin.*—Entire.

*Size and arrangement.*—Lateral petals are similar in size and shape. The base of the petals is fused with column.

*Texture, upper and lower surfaces.*—Smooth.

*Color.*—The main color of both the lower and upper surfaces is RHS 154D. The pattern color is RHS 62C.

Labellum:

*Length.*—About 2 cm.

*Diameter.*—About 1.2 cm.

*Shape.*—Deeply three-lobed with two prominent callosities on the upper surface at the central junction of the lateral lobe and the base of the midlobe.

*Lip whisker.*—Absent.

*Lateral lobe.*—Present.

*Lateral lobe main color* (*upper surface*).—RHS 59B.

*Lateral lobe main color* (*back surface*).—RHS 158B.

*Apical lobe shape.*—Rhombate.

*Labellum margin.*—Entire.

*Base color of the apical lobe.*—RHS 59B.

*Tip color of the apical lobe.*—RHS N74B.

*Labellum main color* (*upper surface*).—RHS 59B.

*Labellum main color* (*back surface*).—RHS 158B.

*Texture, upper and back surfaces.*—Smooth.

*Callosities.*—Present.

*Length of callosities.*—About 0.3-0.35 cm.

*Width of callosities.*—About 0.25-0.3 cm.

*Main color of callosities.*—RHS 11A.

*Spot color of callosities.*—RHS 60C.

Sepals:

*Quantity.*—Three per flower, including one dorsal and two laterals. Appearance — Valvate.

*Dorsal sepal length.*—About 3.1 cm.

*Lateral sepal length.*—About 3.1 cm.

*Dorsal sepal diameter.*—About 2.7 cm.

*Lateral sepal diameter.*—About 2.6 cm. Shape — Oval. Apex — Oval. Base — Oval. Margin — Entire.

*Texture, upper and lower surfaces.*—Smooth.

*Dorsal sepal main color* (*upper and lower surfaces*).—RHS 154D.

*Dorsal sepal pattern color* (*upper and lower surfaces*).—RHS 154D.

*Lateral sepal main color* (*upper and lower surfaces*).—RHS 154D.

*Lateral sepal pattern color* (*upper and lower surfaces*).—RHS 154D.

Peduncles:

*Length.*—About 35 to 40 cm.

*Diameter.*—About 6 mm.

*Strength.*—Upright and strong.

*Texture.*—Smooth, glabrous.

*Color.*—RHS 131A.

Pedicels:

*Length.*—About 15 cm.

*Diameter.*—About 4 mm.

*Aspect.*—About 55° from vertical.

*Strength.*—Strong.

*Texture.*—Smooth, glabrous.

*Color.*—RHS 131A.

Reproductive organs: The stamens, style and stigmas are fused into a column, possessing one terminal anther with pollen grains united into a pollinia, which are covered by an anther cap. The stigma is located under the column behind the pollinia. The ovary is inferior with three carpels presented. The plant has not produced seed.

*Column.*—Length: About 0.9 cm. Diameter: About 4 mm. Color: RHS 3B.

*Stigma.*—Shape: Round. Length: About 3.5 mm. Width: About 3 mm. Color: RHS 3B.

*Pollinia.*—Quantity of pollen masses: Two pollen masses. Diameter: About 1 mm. Color: RHS 23B.

*Ovary.*—Length: About 30 mm. Diameter: About 2.5 mm. Color: RHS 131A.

Root: It takes 30 days for plants growing in tissue culture to initiate roots, and about 6 months to produce a rooted liner.

*Diameter.*—About 6 mm.

*Color.*—RHS 190D.

Disease/pest resistance: Strong disease resistance, but no specific resistance or susceptibility to pests has been observed.

Temperature tolerance: Plants of the new *Phalaenopsis* Orchid have been observed to be tolerant to temperatures from about 15 to 35° C., and flower from 20 to 28° C. in a relative humidty of 60-80%. If the ambient temperature is below 10° C., it is necessary to be aware of chilling injury.

What is claimed is:

1. A new and distinct cultivar of *Phalaenopsis* orchid plant named '*P*. Ho's Colourful Bubbles' as illustrated and described.

* * * * *